United States Patent [19]

Boswell, Jr.

[11] Patent Number: 4,495,196

[45] Date of Patent: Jan. 22, 1985

[54] ANTIINFLAMMATORY 4,5-DIARYL-α-POLYFLUOROALKYL-1H-PYRROLE-2-METHANOLS AND METHOD FOR USE THEREOF

[75] Inventor: George A. Boswell, Jr., Wilmington, Del.

[73] Assignee: E. I. Du Pont de Nemours and Company, Wilmington, Del.

[21] Appl. No.: 294,327

[22] Filed: Aug. 19, 1981

Related U.S. Application Data

[63] Continuation-in-part of Ser. No. 166,807, Jul. 17, 1980, abandoned, which is a continuation-in-part of Ser. No. 159,238, Jun. 20, 1980, abandoned, which is a continuation-in-part of Ser. No. 070,326, Aug. 27, 1979, abandoned.

[51] Int. Cl.³ ............... A61K 31/40; A61K 31/45; C07D 207/323; C07D 213/04

[52] U.S. Cl. .................... 514/427; 546/281; 548/561; 548/562; 424/263; 514/333; 514/343

[58] Field of Search ............... 260/326.5 R; 548/562, 548/561; 424/274, 263; 546/281

[56] References Cited

U.S. PATENT DOCUMENTS

| | | | |
|---|---|---|---|
| 3,197,480 | 7/1965 | England | 260/326.5 |
| 3,709,906 | 1/1973 | Yoshida et al. | 260/326.5 |
| 4,267,184 | 5/1981 | Cherkofsky | 424/263 |

Primary Examiner—Glennon H. Hollrah
Assistant Examiner—D. B. Springer

[57] ABSTRACT 4,5-Diaryl-α-polyfluoroalkyl-1H-pyrrole-2-methanols, such as 4,5-bis (4-fluorophenyl)-α, α-bis (trifluoromethyl)-1H-pyrrole-2-methanol, are useful in treatment of inflammation and relieving pain.

33 Claims, No Drawings

ANTIINFLAMMATORY 4,5-DIARYL-α-POLYFLUOROALKYL-1H-PYRROLE-2-METHANOLS AND METHOD FOR USE THEREOF

CROSS-REFERENCE TO RELATED APPLICATIONS

This application is a continuation-in-part of application Ser. No. 166,807, filed on July 17, 1980 which is a continuation-in-part of application Ser. No. 159,238, filed on June 20, 1980, which is a continuation-in-part of application Ser. No. 070,326, filed on Aug. 27, 1979, all now abandoned.

BACKGROUND OF THE INVENTION

This invention relates to antiinflammatory pyrroles.

J. Szmuszko vicz et al., *J. Med. Chem.*, 9, 527 (1966) describe the synthesis and biological activity of a clinically tested antiinflammatory agent of the formula

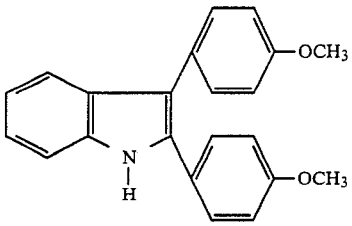

Yoshida, et al., U.S. Pat. No. 3,709,906 discloses 5-alkyl-2,3-diphenylpyrrole derivatives which are useful as antiinflammatory agents.

D. C. England, U.S. Pat. No. 3,197,480 includes disclosure of the compound:

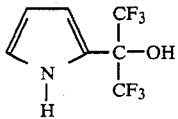

Pharmaceutical use is not disclosed.

There is a continuing need for safe and effective antiinflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited because of toxicity and adverse side-effects. Many produce gastric irritation and other effects, such as changes in blood cells and central nervous system. Adreno-cortical steroids produce gastric irritation and suppresion of normal adrenal function.

In addition to antiinflammatory properties, compounds within the scope of this invention have demonstrated analgesic activity in a test procedure. This additional property is desirable in treatment of arthritis or related diseases; however, the compounds which exhibit this property can be employed solely to alleviate pain.

SUMMARY OF THE INVENTION

This invention relates to compounds of formula I, pharmaceutical compositions containing them, and methods of use of these compounds to treat arthritis and/or to alleviate pain in mammals.

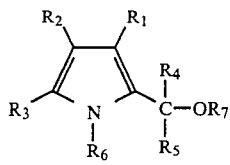

wherein
$R_1$ = H or $C_1$–$C_2$ alkyl;
$R_2$ and $R_3$ independently = 3-pyridyl or

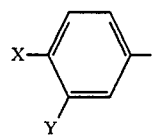

where
$X$ = H, F, Cl, Br, $NO_2$, $C_1$–$C_2$ alkyl, $C_1$–$C_2$ alkoxy, di($C_1$–$C_2$ alkyl)amino or $CH_3S(O)_n$ where $n$ = 0, 1 or 2; and
$Y$ = H, F or Cl;
with the proviso that when Y is F or Cl, then X is F or Cl;
$R_4$ and $R_5$ independently = H, $CF_3$, $CF_2H$, $CFCl_2$, $CF_2Cl$, $CF_2CF_3$, $C_1$–$C_3$ alkyl or $CF_2CF_2CF_3$;
with the provisos (1) that no more than one of $R_4$ or $R_5$ can be selected from the group consisting of H and $C_1$–$C_3$ alkyl, (2) that no more than one of $R_4$ or $R_5$ can be $CF_2CF_3$, and (3) that when one of $R_4$ or $R_5$ is $CF_2CF_3$ then the other of $R_4$ or $R_5$ must be H; or
$R_4$ and $R_5$ taken together = —$CF_2CF_2CFZ$—, where Z = F, Cl or Br;
$R_6$ = H; $C_1$–$C_6$ alkyl; benzyl; or benzyl substituted with F, Cl, Br, $NO_2$ or $CF_3$;
$R_7$ = H; $C_1$–$C_6$ alkyl; benzyl; benzyl substituted with F, Cl, Br, $NO_2$, $CF_3$, $C_1$–$C_2$ alkyl, or $C_1$–$C_2$ alkoxy; ($C_1$–$C_5$ alkyl)

benzoyl; or benzoyl substituted with F, Cl, Br, $NO_2$, $CF_3$, $C_1$–$C_2$ alkyl, or $C_1$–$C_2$ alkoxy; or —$COOR_8$;
$R_8$ = $C_1$–$C_4$ alkyl; phenyl; phenyl substituted with F, Cl, Br, $NO_2$, $CF_3$, $C_1$–$C_2$ alkyl, or $C_1$–$C_2$ alkoxy; benzyl or benzyl substituted with F, Cl, Br, $NO_2$, $CF_3$, $C_1$–$C_2$ alkyl or $C_1$–$C_2$ alkoxy;
with the proviso that $R_6$ cannot be H when $R_7$ is alkanoyl, benzoyl or substituted benzoyl, or $COOR_8$; or
a pharmaceutically suitable acid addition salt where $R_2$ or $R_3$ is 3-pyridyl or X is dialkylamino; or a pharmaceutically suitable metal salt when $R_7$ is H.

Also disclosed are novel intermediates of Formula II useful in preparation of the antiinflammatory compounds of Formula I.

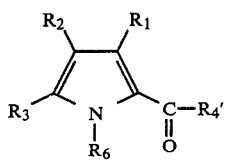

where
$R_1 =$ H or $C_1$-$C_2$ alkyl;
$R_2$ and $R_3$ independently $=$ 3-pyridyl or

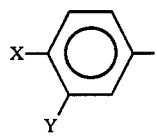

where
$X =$ H, F, Cl, Br, $NO_2$, $C_1$-$C_2$ alkyl, $C_1$-$C_2$ alkoxy, di($C_1$-$C_2$ alkyl)amino, or $CH_3S(O)_n$ where $n = 0$, 1, or 2;
$Y =$ H, F or Cl; with the proviso that when Y is F or Cl, then X is F or Cl;
$R'_4 =$ $CF_3$, $CF_2H$, $CF_2Cl$, $CFCl_2$, $CF_2CF_3$ or $CF_2CF_2CF_3$;
$R_6 =$ H, $C_1$-$C_6$ alkyl, benzyl or benzyl substituted by F, Cl, Br, $NO_2$ or $CF_3$.

Preferred Formula I compounds for utility consideration or ease of synthesis are those in which, independently;
(a) $R_1 =$ H or methyl; or
(b) $R_2$ and $R_3$ independently $=$

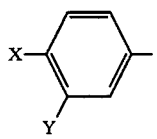

and where $X =$ Cl, F, methoxy or dimethylamino and $Y =$ H; or
(c) $R_4$ and $R_5 = CF_3$; or
(d) $R_6 =$ H or methyl; or
(e) $R_7 =$ H.

Specifically preferred for the same reasons are:
(a) 4,5-bis(4-fluorophenyl)-α,α-bis(trifluoromethyl)-1H-pyrrole-2-methanol;
(b) 4-(4-fluorophenyl)-5-(4-dimethylaminophenyl)-α,α-bis(trifluoromethyl)-1H-pyrrole-2-methanol; and
(c) 4,5-bis(4-fluorophenyl)-1-methyl-α,α-bis(trifluoromethyl)-1H-pyrrole-2-methanol.

Preferred Formula II intermediate compounds for utility consideration or ease of synthesis are those in which, independently
(a) $R_1 =$ H or methyl; or
(b) $R_2$ and $R_3$ independently $=$

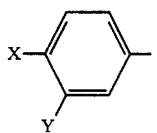

where $X =$ Cl, F or $CH_3O$ and $Y =$ H; or
(c) $R'_4 = CF_3$ or $CF_2CF_3$; or
(d) $R_6 =$ H or methyl.

Specifically preferred for the same reasons are
(a) 1-[4,5-bis(4-methoxyphenyl)-1H-pyrrol-2-yl]-2,2,2-trifluoro-1-ethanone;
(b) 1-[4,5-bis(4-fluorophenyl)-1H-pyrrol-2-yl]-2,2,2-trifluoro-1-ethanone; and
(c) 1-[4,5-bis(4-fluorophenyl)-1H-pyrrol-2-yl]-2,2,3,3,3-pentafluoro-1-propanone.

SYNTHESIS

The compounds of Formula I can be prepared from 2,3-diarylpyrroles. One method of preparation of 2,3-diarylpyrroles involves reaction of substituted α-aminodeoxybenzoins with acetylene diesters, followed by hydrolysis and decarboxylation according to the procedure used by J. Szmuszkovicz, et al., *J. Med. Chem.*, 9, 527 (1966) and by U.S. Pat. No. 3,462,451, the disclosures of which are hereby incorporated by reference, for the synthesis of 2,3-bis(4-methoxyphenyl)pyrrole. (Scheme I).

Scheme I

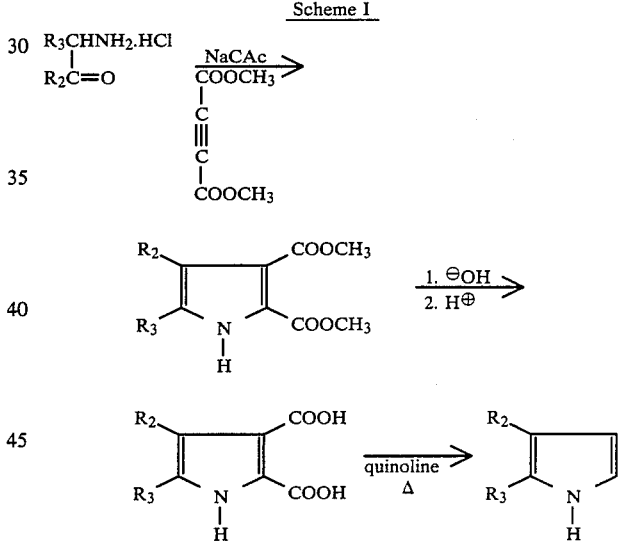

Another method of preparation of 2,3-diarylpyrroles is a modification of the procedure of T. Severin and H. Poehlmann, *Chem. Ber.*, 110, 491 (1977), hereby incorporated by reference, which described the preparation of monoaryl pyrroles. By using substituted desoxybenzoins, the desired 2,3-diarylpyrroles are formed. (Scheme II).

Scheme II

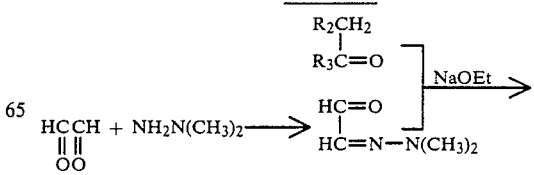

-continued
Scheme II

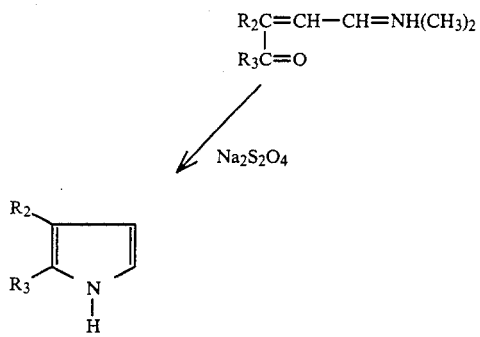

Preparation of 2,3-diaryl-4-alkylpyrroles can be accomplished by several methods. First, 4,5-diarylpyrrole-3-carboxylate esters, prepared, for instance, by the method of A. M. van Leusen, et al., *Tet. Letters,* 5337 (1972) can be reduced to the 2,3-diaryl-4-methylpyrroles by lithium aluminum hydride [following the general procedure of R. L. Hinman and S. Theodoropulos, *J. Org. Chem.,* 28, 3052 (1963)], hereby incorporated by reference.

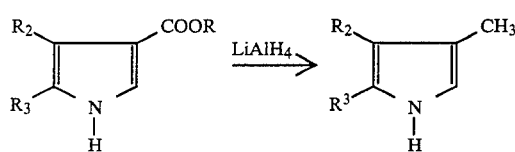

Secondly, 2,3-diaryl-4-alkylpyrroles can be prepared by the general procedure of N. Engel and W. Steglich, *Angew. Chem. Int. Ed. Engl.,* 17, 676 (1978), hereby incorporated by reference, from N-allylcarboxamides.

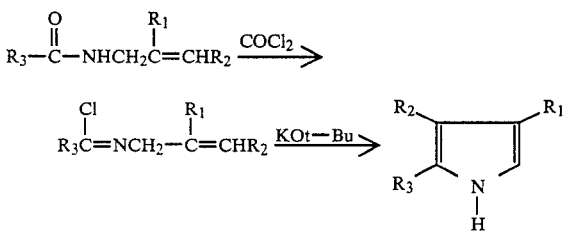

These methods of preparation of 2,3-diarylpyrroles are described in U.S. Pat. No. 4,267,184.

1-Alkyl (or benzyl-2,3-diarylpyrroles can be prepared from the corresponding 2,3-diarylpyrroles by treatment with a strong base, such as sodium hydride, followed by alkylation using an alkyl (or benzyl) halide or other suitable alkylating reagent, such as methyl iodide (L signifies an appropriate leaving group).

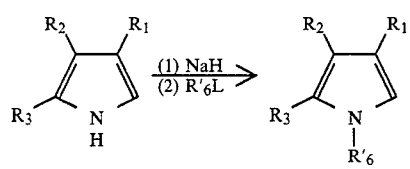

$R'_6 = C_1-C_6$ alkyl, benzyl or substituted benzyl.

Introduction of the α-polyfluoroalkylmethanol group can be accomplished in several ways; first, by reaction of a 2,3-diarylpyrrole with a fluorinated ketone or aldehyde or their various hydrates.

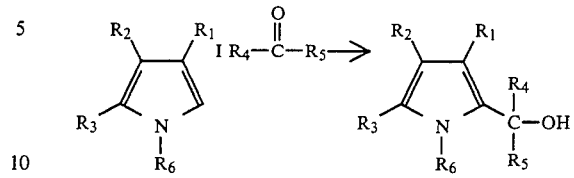

This reaction can be conducted in a sealed pressure reactor at temperature from ambient to 200° C. It can also be conducted in a refluxing solvent such as toluene, in a flask with the fluorinated ketone or aldehyde, such as hexafluoroacetone monohydrate, sesquihydrate or trihydrate or trifluoroacetaldehyde hydrate. Acidic catalysts such as $AlCl_3$, $BF_3$, p-toluenesulfonic acid or trifluoroacetic acid can be used but are not required. Reaction times are usually 4–24 hours. The use of hexafluoroacetone trihydrate in refluxing toluene without catalyst is preferred.

Secondly, addition of Grignard reagents to 1-(4,5-diaryl-1H-pyrrol-2-yl)-polyfluoro-1-alkanones, can give compounds of Formula I. This reaction is particularly useful when $R_5$ is $C_1-C_3$ alkyl.

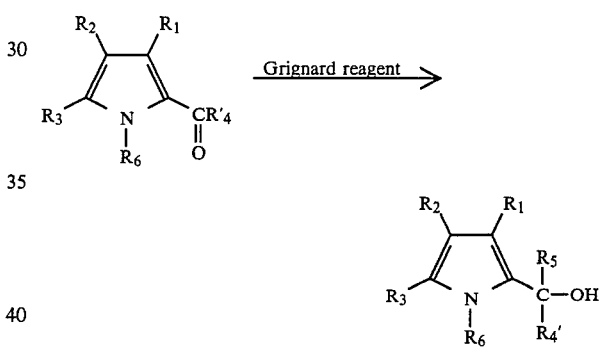

1-(4,5-Diaryl-1H-pyrrol-2-yl)-polyfluoro-1-alkanones can be prepared from the corresponding 2,3-diarylpyrroles, by treatment with a polyfluorinated acid anhydride in the absence or presence of a base, such as N,N-dimethylaniline. The reaction can be run in any solvent which is inert to the reactants, at temperatures from −78° C. to the boiling point of the solvent, preferably at 0° C.

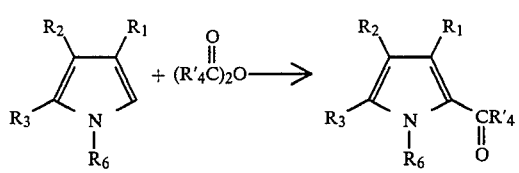

Alternatively, the $R'_6$ group can be introduced after the polyfluoroacyl group has been introduced into compounds with $R_6=H$. The 1-(4,5-diaryl-1H-pyrrol-2-yl)-polyfluoro-1-alkanone (with $R_6=H$) is contacted with a strong base, such as sodium hydride, followed by alkylation using an alkyl (or benzyl) halide or other suitable alkylating reagent, e.g., methyl iodide (L signifies an appropriate leaving group, such as halide or sulfonate).

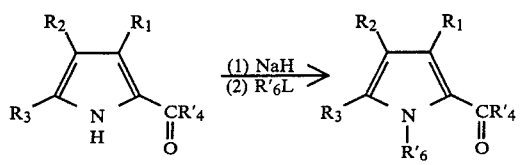

Thirdly, reaction of 1-(4,5-diaryl-1H-pyrrol-2-yl)-polyfluoro-1-alkanones with reducing agents, such as NaBH$_4$ or the like, can give compounds of Formula I where R$_5$=H.

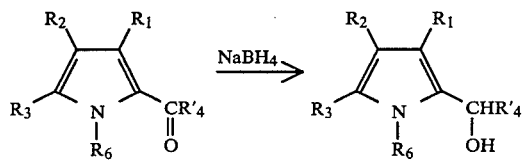

Fourthly, compounds of Formula I with R$_6$ and/or R$_7$≠H can be prepared by alkylation of the corresponding compounds with R$_6$ and/or R$_7$=H. Alkylation can occur on either or both the NH or OH, depending on the conditions of the reaction. Often mixtures of alkylated products are obtained. These alkylations can be conducted in the presence of a base, such as potassium carbonate, pyridine, triethylamine, potassium-t-butoxide, sodium hydride or the like. (L signifies an appropriate leaving group).

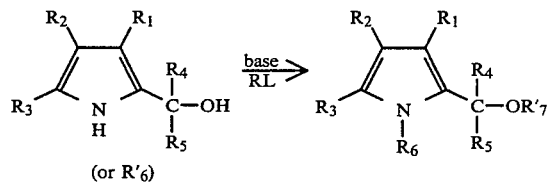

(R'$_7$=H, alkyl, benzyl or substituted benzyl)

Fifthly, compounds of Formula I with R$_7$=alkanoyl, benzoyl or substituted benzoyl, or COOR$_8$ can be prepared from the corresponding compound with R$_7$=H by treatment with a base followed by reaction with an acid chloride, or alternatively, by direct reaction with an acid anhydride.

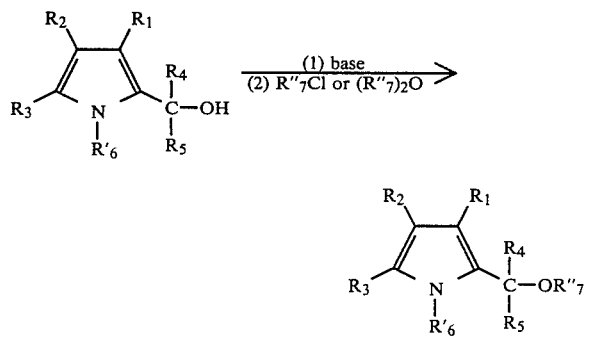

R"$_7$=alkanoyl, benzoyl, substituted benzoyl or COOR$_8$

Pharmaceutically suitable salts of the compounds of formula I can be of two types. First, when one or both aryl groups is a dialkylaminophenyl or a 3-pyridyl group, acid addition salts can be prepared by treatment of the free base I with the appropriate acid. Second, pharmaceutically suitable metal salts (forming the salt of the acidic OH) can be prepared by treatment of compounds of the formula I (with R$_7$=H) with strong bases such as hydroxides, alkoxides, or the like.

In the following examples, all parts are by weight and temperatures are in degrees centigrade unless otherwise specified.

PREPARATION 1

2,3-Diphenylpyrrole (Method A)

A. Dimethyl 4,5-diphenylpyrrole-2,3-dicarboxylate

In a 2 l RB 3-neck flask with mechanical stirrer and condenser was placed 76.7 g (0.31 mole) of desyl amine hydrochloride [Pschorr et al, *Chem. Ber.*, 35, 2740 (1902)], 750 ml methanol, 88 g (0.62 mole) dimethyl acetylenedicarboxylate (freshly distilled) and 61 g (0.75 mole) anhydrous sodium acetate. The mixture was heated at reflux for two hours. Then another 44 g (0.31 mole) of dimethyl acetylenedicarboxylate was added, and heating continued another two hours. While the reaction mixture was still at reflux, concentrated hydrochloric acid (~60 ml, to pH~2) was added dropwise. The mixture was heated at reflux another hour, then poured into 2 l water containing 200 ml 10% sodium bicarbonate solution. With stirring, more sodium bicarbonate was added until the solution was neutral. The gummy solid which precipitated was collected and washed with water. Trituration of this gummy material with ~500 ml of 50% aqueous ethanol gave a tan powdery solid, which was recrystallized from ~85% aqueous ethanol to give 65.5 g (63%) of white crystals, m.p. 191°–2° [Lit. m.p. 185°–7°; J. B. Hendrickson et al, *J. Am. Chem. Soc.*, 86, 107 (1964)].

B. 4,5-Diphenylpyrrole-2,3-dicarboxylic Acid

To a mixture of 57.5 g (0.172 mole) of dimethyl 4,5-diphenylpyrrole-2,3-dicarboxylate in 350 ml methanol was added a solution of 71 g (1.78 mole) of sodium hydroxide in 350 ml water. The mixture was heated at reflux for two hours, then cooled in an ice bath. The insoluble white crystals were collected and washed with cold methanol to give the bis sodium salt of the product. The still damp solid was dissolved in 1 l cold water and acidified with conc. hydrochloric acid. The precipitated product was collected by filtration, washed with water containing ~1% hydrochloric acid, then air dried and finally dried in a vacuum oven at 100° to give 50.0 g (95%) of white solid, m.p. 216°–218° (dec., depends on heating rate).

C. 2,3-Diphenylpyrrole (Method A)

A mixture of 20 g (0.065 mole) of 4,5-diphenylpyrrole-2,3-dicarboxylic acid in 80 ml quinoline was heated at reflux in an oil bath (bath ~230°) until gas evolution stopped (approx. one-half hour). The reaction mixture was cooled and most of the quinoline was removed by distillation (bp 58° @ 0.2 mm). The partially crystalline residue was chromatographed on 300 g Silic AR CC-7, eluting with toluene to give 12 g (85%) of faintly pink 2,3-diphenylpyrrole which could be further purified by recrystallization from ethanol/water or by sublimation (~125° @ 0.2 mm) to give white solid, m.p. 132°–3°.

Anal. Calcd. for C$_{16}$H$_{13}$N: C, 87.64; H, 5.98; N, 6.39. Found: C, 87.99; H, 5.86; N, 6.50.

PREPARATION 2

2,3-Diphenylpyrrole (Method B)

A. Glyoxal mono(dimethylhydrazone) was prepared by the procedure of T. Severin and H. Poehlmann, *Chem. Ber.*, 110, 491 (1977) to give 36.1 g (80%) of pale yellow liquid, bp 109° (22 mm); lit. bp 90° (16 mm).

B. 4-Dimethylhydrazono-1,2-diphenyl-2-buten-1-one

To a mixture of 19.6 g (0.1 mole) desoxybenzoin and 10 g (0.1 mole) of glyoxal mono(dimethylhydrazone) in 100 ml ethanol was added dropwise a solution of sodium ethoxide prepared by dissolving 2.3 g (0.1 mole) sodium metal in 100 ml ethanol. The mixture was heated at reflux for one-half hour. TLC (90/10, toluene/ethyl acetate) showed a small amount of starting desoxybenzoin, so 2.0 g (0.02 mole) of additional glyoxal mono(dimethylhydrazone) was added. Heating was continued another two hours. TLC at this time showed no starting material, and two clean close yellow product spots (isomers). The mixture was poured into 1 l ice water then extracted with methylene chloride. The organic extracts were dried and concentrated on a rotary evaporator to give 28.7 g (100%) of yellow oil. The NMR showed the presence of two major N(CH$_3$)$_2$ containing materials (product isomers). The crude oil crystallized from isopropanol to give one pure isomer of product, 13.4 g (48%), pale yellow crystals, m.p. 131°-2°.

Anal. Calcd. for C$_{18}$H$_{18}$N$_2$O: C, 77.67; H, 6.52; N, 10.06. Found: C, 77.44; H, 6.46; N, 10.17.

C. 2,3-Diphenylpyrrole (Method B)

A mixture of 3.1 g (0.011 mole) of 4-dimethylhydrazono-1,2-diphenyl-2-buten-1-one, 11.2 g (0.064 mole) sodium hydrosulfite in 75 ml ethanol and 37.5 ml water was heated at reflux for three hours. The mixture was cooled and poured into 300 ml ice water. The white crystalline produce was collected, washed with water and air dried to give 1.9 g (79%), m.p. 130°-1°, identical to product obtained via the decarboxylation, Method A.

PREPARATION 3

2,3-Diphenyl-4-methylpyrrole

A. Ethyl 4,5-diphenylpyrrole-3-carboxylate was prepared by a procedure similar to that used by A. M. van Leusen et al., *Tet. Letters*, 5337 (1972) for the preparation of the methyl ester. The ethyl ester was obtained as a white solid, m.p. 207°–208.5° (methyl cyclohexane/toluene).

Anal. Calcd. for C$_{19}$H$_{17}$NO$_2$: C, 78.33; H, 5.88; N, 4.81. Found: C, 77.92; 77.90; H, 5.87; 5.88; N, 4.60; 4.62.

B. 2,3-Diphenyl-4-methylpyrrole

To a stirred slurry of 0.76 g (20 mmoles) of lithium aluminum hydride in 25 ml. THF was added dropwise a solution of 0.58 g (2 mmoles) of ethyl 4,5-diphenylpyrrole-3-carboxylate in 5 ml THF. The mixture was heated at reflux overnight. After cooling, 0.8 ml water, 2.4 ml 15% sodium hydroxide solution and 0.8 ml water were added dropwise. The solids were removed by filtration and the filtrate concentrated by rotary evaporation. The crystalline residue was purified by chromatography on 50 g Silic AR CC-7, eluting with hexane/toluene (90/10) to give 0.25 g of product, m.p. 163°-4°.

Anal. Calcd. for C$_{17}$H$_{15}$N: C, 87.51; H, 6.48; N, 6.00. Found: C, 87.77; H, 6.60; N, 5.89.

PREPARATION 4

2,3-Bis(4-fluorophenyl)-4-methyl-1H-pyrrole

A. 3-(4-Fluorophenyl)-2-methyl-2-propen-1-al

To a solution of 124 g (1 mole) of 4-fluorobenzaldehyde and 8 g (0.143 mole) of potassium hydroxide in 500 ml ethanol at room temperature was added dropwise a solution of 52.2 g (0.9 mole) of propionaldehyde in 100 ml ethanol. After stirring for 0.5 hour, the mixture was acidified with acetic acid and concentrated by rotary evaporation. The residue was partitioned between methylene chloride and water. The aqueous layer was extracted three times with additional methylene chloride. The combined organic layers were dried and concentrated. Distillation through a 12-inch vacuum jacketed column gave 113.5 g (77%) of pale yellow low-melting crystalline product, b.p. 70°-72° C. (0.4–0.7 mm).

Anal. Calcd. for C$_{10}$H$_9$FO: C, 73.16; H, 5.53; Found: C, 72.89, 72.72; H, 5.66, 5.46.

B. 3-(4-Fluorophenyl)-2-methyl-2-propen-1-ol

To a solution of 113 g (0.69 mole) of 3-(4-fluorophenyl)-2-methyl-2-propen-1-al in 800 ml ethanol at 10° C. was added in portions 13.1 g (0.345 mole) of sodium borohydride. After the addition was complete, the reaction mixture was stirred at room temperature overnight. The mixture was cooled in an ice bath while 350 ml of 1N hydrochloric acid was added dropwise to give a final pH of ~7. The mixture was diluted with 500 ml water and extracted three times with methylene chloride. The organic extracts were dried and concentrated and the residue distilled to give 56.1 g (49%) of colorless liquid, b.p. 68°-70° C. (0.15 mm).

Anal. Calcd. for C$_{10}$H$_{11}$FO: C, 72.27; H, 6.67; Found: C, 72.30, 72.38; H, 6.61, 6.62.

C. 1-Chloro-3-(4-fluorophenyl)-2-methyl-2-propene

To a solution of 53.6 g (0.32 mole) of 3-(4-fluorophenyl)-2-methyl-2-propen-1-ol in 100 ml methylene chloride was added dropwise a solution of 57.1 g (0.48 mole) of thionyl chloride in 100 ml methylene chloride. The reaction mixture was stirred at room temperature for 2 hours, then concentrated by rotary evaporation. The product was checked by NMR, then used crude in the reaction with ammonia.

D. 3-(4-Fluorophenyl)-2-methyl-2-propen-1-amine

A quantity of 59.1 g (0.32 mole) of 1-chloro-3-(4-fluorophenyl)-2-methyl-2-propene and 500 ml ethanol was loaded in a pressure vessel. The vessel was cool-evacuated and 100 g of ammonia was added. The mixture was heated at 95° for 3 hours with shaking. The vessel was cooled, vented and the contents rinsed out with ethanol. The mixture was concentrated by rotary evaporation. The residue was diluted with 1.5 l water and acidified with concentrated hydrochloric acid. This mixture was filtered to remove some insoluble solid (undissolved amine hydrochloride). The aqueous filtrate was extracted with ether to remove any non-basic impurities. The aqueous layer was combined with the insoluble solid and made basic with 5% sodium hydroxide solution. This was then extracted with ether and the ether extracts were dried and concentrated. Distillation of the residue gave 22.8 g (43%) of colorless liquid, b.p. 57° C. (0.2 mm).

Anal. Calcd. for $C_{10}H_{12}FN$: C, 72.70; H, 7.32; N, 8.48; Found: C, 72.67, 72.59; H, 7.48, 7.53; N, 8.31.

E. 4-Fluoro-N-[3-(4-fluorophenyl)-2-methyl-2-propenyl]-benzamide

To a vigorously stirred mixture of 19.8 g (0.12 mole) of 3-(4-fluorophenyl)-2-methyl-2-propen-1-amine and 30.2 g (0.36 mole) of sodium bicarbonate in 500 ml water at 5° C. was added dropwise 22.2 g (0.14 mole) of 4-fluorobenzoyl chloride. The mixture was stirred another 3 hours at 5° C. then at room temperature overnight. The white solid which had formed was collected, washed with saturated sodium bicarbonate solution, then with water, then with hexane, then air dried to give 33.4 g (97%) of product, m.p. 107°–109° C.

Anal. Calcd. for $C_{17}H_{15}F_2NO$: C, 71.07; H, 5.26; N, 4.88; Found: C, 70.85; H, 5.48; N, 4.70.

F. 2,3-Bis(4-fluorophenyl)-4-methyl-1H-pyrrole

Using the general procedure of N. Engel and W. Steglich, *Angew. Chem. Int. Ed. Engl.*, 17, 676 (1978), to a slurry at room temperature of 28.7 g (0.1 mole) of 4-fluoro-N-[3-(4-fluorophenyl)-2-methyl-2-propenyl]-benzamide in 100 ml toluene containing 1 ml DMF, stirred under nitrogen, with a dry ice condenser attached, was added dropwise a solution of 39.6 g (28.3 ml, 0.4 mole) of phosgene in 100 ml toluene. The mixture was warmed slightly with a heat gun, then stirred at room temperature overnight. The solution was concentrated by rotary evaporation to give a yellow oil. This was dissolved in 100 ml dry THF (small amount of insoluble solid removed by decanting the solution) and the solution was added dropwise to a cool (15°) solution of 33.5 g (0.3 mole) of potassium t-butoxide in 150 ml DMSO. The dark purple solution was stirred at ~20° C. for 1 hour, then was poured into 1 liter ice water. This was extracted with ether and the ether layers backwashed with water. The ether layer was dried and concentrated and the residue was chromatographed on 900 g of silica gel, eluting with hexane containing 10–40% toluene, to give, after recrystallization from methyl cyclohexane, 10.8 g (40%) of white product, m.p. 126°–7° C.

Anal. Calcd. for $C_{17}H_{13}F_2N$: C, 75.82; H, 4.87; N, 5.20; Found: C, 75.87; H, 4.85; N, 5.13.

Other 2,3-diarylpyrroles prepared by these procedures are given in Table I.

TABLE I 2,3-Diarylpyrroles

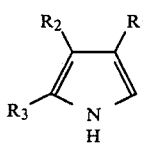

| Preparation | $R_2$ | $R_3$ | $R_1$ | m.p. °C. |
|---|---|---|---|---|
| 5 | 4-ClC$_6$H$_4$ | 4-ClC$_6$H$_4$ | H | 124–127 |
| 6 | 4-FC$_6$H$_4$ | 4-FC$_6$H$_4$ | H | 119.5–120.5 |
| 7 | C$_6$H$_5$ | 3,4-diClC$_6$H$_3$ | H | 112–113 |
| 8 | 4-FC$_6$H$_4$ | 4-BrC$_6$H$_4$ | H | 129–130 |
| 9 | C$_6$H$_5$ | 3-pyridyl | H | 190–192 |
| 10 | 4-CH$_3$OC$_6$H$_4$ | 4-CH$_3$OC$_6$H$_4$ | H | oil |
| 11 | 4-CH$_3$C$_6$H$_4$ | 4-CH$_3$C$_6$H$_4$ | H | 128–129 |
| 12 | 4-FC$_6$H$_4$ | 4-(CH$_3$)$_2$NC$_6$H$_4$ | H | 200–201 |

TABLE I-continued 2,3-Diarylpyrroles

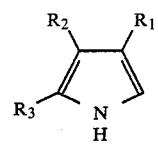

| Preparation | $R_2$ | $R_3$ | $R_1$ | m.p. °C. |
|---|---|---|---|---|
| 13 | 4-FC$_6$H$_4$ | 3-pyridyl | H | 173–174 |
| 14 | 4-FC$_6$H$_4$ | 4-CH$_3$SC$_6$H$_4$ | H | 164–165 |
| 15 | 4-FC$_6$H$_4$ | 4-CH$_3$SO$_2$C$_6$H$_4$ | H | 268–270 |

EXAMPLE 1

4,5-Bis(4-chlorophenyl)-α,α-bis(trifluoromethyl)-1H-pyrrole-2-methanol

A mixture of 2.9 g (0.01 mole) of 2,3-bis(4-chlorophenyl)-1H-pyrrole and 2.5 g (0.011 mole) of hexafluoroacetone trihydrate in 50 ml toluene was heated at reflux overnight. The mixture was concentrated on a rotary evaporation and the solid residue was chromatographed on 200 g silica gel (eluting with toluene), then recrystallized from hexane to give 3.8 g of product, m.p. 144°–145° C.

Anal. Calcd. for $C_{19}H_{11}Cl_2F_6NO$: C, 50.24; H, 2.44; N, 3.08; Found: C, 50.05; H, 2.65; N, 2.84.

Other 4,5-diaryl-α,α-bis(trifluoromethyl)-1H-pyrrole-2-methanols that can be prepared by this procedure are given in Table II.

TABLE II 4,5-Diaryl-α,α-bis(trifluoromethyl)-1H—pyrrole-2-methanols

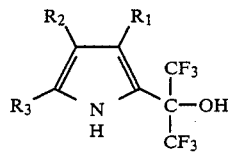

| Example | $R_2$ | $R_3$ | $R_1$ | mp °C. |
|---|---|---|---|---|
| 2 | C$_6$H$_5$ | C$_6$H$_5$ | H | 96–97 |
| 3 | 4-FC$_6$H$_4$ | 4-FC$_6$H$_4$ | H | 112–113 |
| 4 | C$_6$H$_5$ | 3,4-diClC$_6$H$_3$ | H | 119–120 |
| 5 | 4-FC$_6$H$_4$ | 4-BrC$_6$H$_4$ | H | 129–130 |
| 6 | 4-FC$_6$H$_4$ | 4-FC$_6$H$_4$ | CH$_3$ | 154–155.5 |
| 7 | C$_6$H$_5$ | 3-pyridyl | H | 201–203 (HCl salt m.p. 228–230 dec.) |
| 8 | 4-CH$_3$OC$_6$H$_4$ | 4-CH$_3$OC$_6$H$_4$ | H | 130–131 |
| 9 | 4-CH$_3$C$_6$H$_4$ | 4-CH$_3$C$_6$H$_4$ | H | 109–109.5 |
| 10 | 4-FC$_6$H$_4$ | 4-(CH$_3$)$_2$NC$_6$H$_4$ | H | 136–137 (HCL salt, m.p. 225° dec.) |
| 11 | 4-FC$_6$H$_4$ | 3-pyridyl | H | 227–229 |
| 12 | 4-FC$_6$H$_4$ | 4-CH$_3$SC$_6$H$_4$ | H | 167–168 |
| 13 | 4-FC$_6$H$_4$ | 4-CH$_3$SO$_2$C$_6$H$_4$ | H | 257–258 |
| 14 | 4-C$_2$H$_5$C$_6$H$_4$ | 4-C$_2$H$_5$C$_6$H$_4$ | C$_2$H$_5$ | |
| 15 | 4-FC$_6$H$_4$ | 4-NO$_2$C$_6$H$_4$ | H | |

Following the procedure given in Example 1 with the appropriate 2,3-diarylpyrrole and polyfluorinated ketone, the following 4,5-diaryl-α,α-bis(polyfluoromethyl)-1H-pyrrole-2-methanols can be prepared (Table III).

TABLE III 4,5-Diaryl-α,α-bis(polyfluoromethyl)-1H—pyrrole-2-methanols

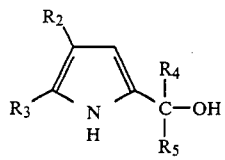

| Example | R$_2$ | R$_3$ | R$_4$ | R$_5$ | m.p. °C. |
|---|---|---|---|---|---|
| 16 | 4-FC$_6$H$_4$ | 4-FC$_6$H$_4$ | —CF$_2$CF$_2$CF$_2$— | | 93-94° |
| 17 | 4-FC$_6$H$_4$ | 4-FC$_6$H$_4$ | CF$_2$Cl | CF$_2$Cl | 124-125° |
| 18 | 4-FC$_6$H$_4$ | 4-FC$_6$H$_4$ | CF$_2$H | CF$_3$ | 113-115° |
| 19 | 4-FV$_6$H$_4$ | 4-FC$_6$H$_4$ | CF$_2$Cl | CF$_3$ | 107-108° |
| 20 | 4-FC$_6$H$_4$ | 4-FC$_6$H$_4$ | —CF$_2$CF$_2$CFCl— | | 114-115° |
| 21 | 4-FC$_6$H$_4$ | 4-FC$_6$H$_4$ | —CF$_2$CF$_2$CFBr— | | 121-122° |
| 22 | 4-FC$_6$H$_4$ | 4-FC$_6$H$_4$ | CF$_2$Cl | CFCl$_2$ | 109-110° |
| 23 | 4-C$_2$H$_5$OC$_6$H$_4$ | 4-C$_2$H$_5$OC$_6$H$_4$ | CF$_2$H | CF$_2$H | |
| 24 | 4-ClC$_6$H$_4$ | 4-ClC$_6$H$_4$ | CF$_2$Cl | CF$_2$Cl | |
| 25 | 4-FC$_6$H$_4$ | 4-CH$_3$SO$_2$C$_6$H$_4$ | CF$_2$H | CF$_3$ | |
| 26 | 4-(C$_2$H$_5$)$_2$NC$_6$H$_4$ | 4-FC$_6$H$_4$ | CF$_2$H | CF$_2$Cl | |
| 27 | 3-F, 4-ClC$_6$H$_3$ | 4-CH$_3$OC$_6$H$_4$ | CF$_2$Cl | CF$_3$ | |

EXAMPLE 28

4,5-Bis(4-fluorophenyl)-1-methyl-α,α-bis(trifluoromethyl-1H-pyrrole-2-methanol

A. 2,3-Bis(4-fluorophenyl)-1-methyl-1H-pyrrole

To a mixture of 1.5 g (0.038 mole) of 60% sodium hydride dispersion and 100 ml DMSO was added dropwise a solution of 5.1 g (0.02 mole) of 2,3-bis(4-fluorophenyl)-1H-pyrrole in 25 ml DMSO. After the mixture was stirred one hour at room temperature, 5.6 g (0.04 mole) of methyl iodide was added dropwise. The mixture was stirred at room temperature overnight, then poured into water and extracted with ether. The ether extracts were backwashed with water three times, then dried and concentrated. The crude solid was recrystallized from hexane to give 4.3 g of product, m.p. 129°-129.5°.

Anal. Calcd for: C$_{17}$H$_{13}$F$_2$N: C, 75.82; H, 4.87; N, 5.20. Found: C, 75.89, 75.78; H, 4.98, 4.97; N, 5.18, 5.10.

B. 4,5-Bis(4-fluorophenyl)-1-methyl-α,α-bis(trifluoromethyl)-1H-pyrrole-2-methanol A mixture of 4.0 g (0.015 mole) of 2,3-bis(4-fluorophenyl)-1-methyl-1H-pyrrole and 3.7 g (0.017 mole) of hexafluoroacetone trihydrate in 75 ml toluene was heated at reflux overnight. Another 3.7 g of hexafluoroacetone trihydrate was added and the mixture was heated at reflux overnight again. An additional 2.0 g of hexafluoroacetone trihydrate was added and the mixture was heated at reflux another eight hours. The mixture was washed twice with water, then the organic layer was dried and concentrated. The crude product was purified by chromatography on silica gel, eluting with hexane/toluene mixtures to give, after recrystallization from hexane, 4.8 g of product, m.p. 130°-131°.

Anal. Calcd. for C$_{20}$H$_{13}$F$_8$NO: C, 55.18; H, 3.01; N, 3.22. Found: C, 55.15, 55.24; H, 3.03, 3.00; N, 3.29, 3.23.

EXAMPLE 29

4,5-Bis(4-fluorophenyl)-α-(trifluoromethyl)-1H-pyrrole-2-methanol

A mixture of 2.55 g (0.01 mole) of 2,3-bis(4-fluorophenyl)-1H-pyrrole and 1.3 g (0.011 mole) of trifluoroacetaldehyde hydrate in 75 ml toluene was heated at reflux for 3.5 hours. The mixture was concentrated on a rotary evaporator. The residue was purified by chromatography on silica gel to give 1.9 g of product, m.p. 121°-122°.

Anal. Calcd. for C$_{18}$H$_{12}$F$_5$NO: C, 61.20; H, 3.42; N, 3.96. Found: C, 61.24; H, 3.39; N, 4.12.

EXAMPLE 30

4,5-Bis(4-methoxyphenyl)-α-(trifluoromethyl)-1H-pyrrole-2-methanol

A. 1-[4,5-Bis(4-methoxyphenyl)-1H-pyrrol-2-yl]-2,2,2-trifluoro-1-ethanone

To a stirred solution of 2.5 g trifluoroacetic anhydride in 30 ml ether at 0° was added dropwise a solution of 2.8 g (0.01 mole) of 2,3-bis(4-methoxyphenyl)-1H-pyrrole and 1.5 g of N,N-dimethyl aniline in 20 ml ether. The mixture was stirred one hour at 0°, then diluted with more ether and washed with water, 1N hydrochloric acid, then water again. The organic layer was dried and concentrated. The residue was purified by chromatography on silica gel, eluting with toluene, to give, after recrystallization from methylcyclohexane, 2.2 g of product, m.p. 185°-186.5°.

Anal. Calcd. for C$_{20}$H$_{16}$F$_3$NO$_3$: C, 64.00; H, 4.30; N, 3.73. Found: C, 64.35, 64.03; H, 4.41, 4.22; N, 3.61, 3.70.

B. 4,5-Bis(4-methoxyphenyl)-α-(trifluoromethyl)-1H-pyrrole-2-methanol

To a stirred mixture of 1.9 g (0.005 mole) of 1-[4,5-bis(4-methoxyphenyl)-1H-pyrrol-2-yl]-2,2,2-trifluoro-1-ethanone and 25 ml ethanol at 0° was added 0.4 g (0.01 mole) of sodium borohydride all at once. The mixture was stirred at 0° 0.5 hour, then at room temperature 1 hour. The mixture was chilled in an ice bath and 40 ml of 1N hydrochloric acid was added dropwise. The mixture was poured into water and extracted with methylene chloride. The organic layers were dried and concentrated. The crude solid was triturated with methylcyclohexane and collected to give 1.6 g of product, m.p. 84°-86°.

EXAMPLE 31

4,5-Bis(4-methoxyphenyl)-α-methyl-α-(trifluoromethyl)-1H-pyrrole-2-methanol

A solution of 3.8 g (0.01 mole) of 1-[4,5-bis(4-methoxyphenyl)-1H-pyrrol-2-yl]-2,2,2-trifluoro-1-ethanone in 20 ml of THF was added dropwise to the Grignard reagent formed from 0.6 g (0.025 mole) of magnesium turnings and 3.6 g (0.025 mole) of methyl iodide in 30 ml ether. The mixture was stirred overnight at room temperature. Then 20 ml of saturated aqueous ammonium chloride was added dropwise. The mixture was transferred to a separatory funnel with 100 ml of 1N hydrochloric acid. The aqueous mixture was extracted with ether. The ether extracts were dried and concentrated and the residue was purified first by elution chromatography (toluene/ethyl acetate: 90/10), then by preparative HPLC to give 1.6 g of product, m.p. 111°–112°.

Anal. Calcd. for $C_{21}H_{20}F_3NO_3$: C, 64.44; H, 5.15; N, 3.58. Found: C, 64.76, 64.77, H, 5.16, 5.17; N, 3.48, 3.39.

EXAMPLE 32

2,3-Bis(4-fluorophenyl)-1-methyl-5-[2,2,2-trifluoro-1-methoxy-1-(trifluoromethyl)ethyl]-1H-pyrrole A mixture of 2.1 g (0.005 mole) of 4,5bis(4-fluorophenyl)-α,α-bis(trifluoromethyl)-1H-pyrrole-2-methanol, 1.4 g anhydrous potassium carbonate and 0.9 g (0.006 mole) of methyl iodide in 25 ml DMF was stirred at room temperature overnight. Another 1.4 g of potassium carbonate and 0.3 g of methyl iodide was added and stirring was continued another two hours. The mixture was poured into water and extracted with ether. The ether layers were backwashed with water three times, then dried and concentrated. The residue was purified by chromatography on silica gel, eluting with hexane/toluene (90/10) to give 1.7 g of the O,N-dimethylated product, m.p. 133°–134° (from ethanol/water). The infrared and nmr spectrum were consistent with the structure.

Anal. Calcd. for $C_{21}H_{15}F_8NO$: C, 56.13; H, 3.36; N, 3.12. Found: C, 56.01, 56.17; H, 3.49, 3.82; N, 3.20, 3.10.

Eluted with toluene was the O-methylated product, 2,3-bis(4-fluorophenyl)-5-[2,2,2-trifluoro-1-methoxy-1-(trifluoromethyl)ethyl]-1H-pyrrole, 0.12 g, m.p. 108°–110° (from ethanol/water). The infrared and nmr spectra were consistent with the structure.

Anal. Calcd. for $C_{20}H_{13}F_8NO$: C, 55.18; H, 3.01; N, 3.22. Found: C, 55.61, 55.81; H, 3.07, 3.06; N, 3.19, 3.19.

EXAMPLE 33

2,3-Bis(4-fluorophenyl)-5-[2,2,2-trifluoro-1-(phenylmethoxy)-1-(trifluoromethyl)ethyl]-1H-pyrrole Prepared by a procedure similar to that above, employing α-bromotoluene in place of methyl iodide, there was obtained the O-benzylated product, named above, obtained as an oil after purification by preparative HPLC.

Mass Spectrum: Calcd for $C_{26}H_{17}F_8NO$: 511.1181. Found: 511.1192.

EXAMPLE 34

4,5-Bis(4-fluorophenyl)-1-methyl-α,α-bis(trifluoromethyl)-1H-pyrrole-2-methanol, Acetate A mixture of 2.2 g (5 mmoles) of 4,5-bis(4-fluorophenyl)-1-methyl-α,α-bis(trifluoromethyl-1H-pyrrole-2-methanol and 50 ml of acetic anhydride was heated at reflux for 4 hours. The mixture was cooled and concentrated by rotary evaporation under reduced pressure. The residue was purified by preparative HPLC on silica gel, eluting with hexane/toluene (50/50). The 1.2 g of product so obtained was combined with 0.6 g of product from another preparation and recrystallized from hexane to give 1.0 g of white crystalline product, m.p. 102°–103°.

Anal. Calcd. for $C_{22}H_{15}F_8NO_2$: C, 55.36; H, 3.17; N, 2.93. Found: C, 55.48; H, 3.29; N, 2.92.

EXAMPLE 35

4,5-Bis(4-fluorophenyl)-1-methyl-α,α-bis(trifluoromethyl)-1H-pyrrole-2-methanol, Benzoate A quantity of 0.85 g (7.5 mmoles)) of potassium t-butoxide was added to a stirred solution of 2.2 g (5 mmoles) of 4,5-bis(4-fluorophenyl)-1-methyl-α,α-bis(trifluoromethyl)-1H-pyrrole-2-methanol in 50 ml glyme at 0°. After the mixture was stirred for 15 minutes, 1.1 g (7.5 mmoles) of benzoyl chloride in 25 ml of glyme was added dropwise. The mixture was stirred at 0° for three hours, then at room temperature for one hour. The mixture was poured into water and extracted with ether. The ether extracts were dried and concentrated to give the crude product as a solid. This was purified by preparative HPLC on silica gel, eluting with 50/50 hexane/toluene to give purified product. This was combined with 0.6 g of product from another preparation and recrystallized from hexane/methylcyclohexane to give 2.4 g of product, m.p. 154°–155°.

Anal. Calcd. for $C_{27}H_{17}F_8NO_2$: C, 60.12; H, 3.18; N, 2.60. Found: C, 59.90; H, 3.36; N, 2.46.

EXAMPLE 36

4,5-Bis(4-fluorophenyl)-1-methyl-α,α-bis(trifluoromethyl)-1H-pyrrole-2-methanol, Methylcarbonate Prepared by a procedure similar to that above, employing methyl chloroformate in place of benzoyl chloride, there was obtained the methyl carbonate ester, named above, obtained as an oil, after purification by preparative HPLC. The IR, proton and fluorine NMR were consistent with the desired structure.

Mass spectrum: Calcd for $C_{22}H_{15}F_8NO_3$: 493.0923; Found: 493.0920.

Following the procedures given in Examples 1–36, the following 4,5-diaryl-α-polyfluoroalkyl-1H-pyrrole-2-methanols can be prepared (Table IV).

TABLE IV
4,5-Diaryl-α-polyfluoroalkyl-1H—pyrrole-2-methanols

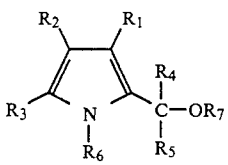

| Example | $R_1$ | $R_2$ | $R_3$ | $R_4$ | $R_5$ | $R_6$ | $R_7$ | Melting Point °C. |
|---|---|---|---|---|---|---|---|---|
| 37 | H | 4-FC$_6$H$_4$ | 4-FC$_6$H$_4$ | CF$_2$CF$_3$ | H | H | H | 135–136° |
| 38 | H | 4-FC$_6$H$_4$ | 4-FC$_6$H$_4$ | CF$_2$CF$_3$ | CH$_3$ | H | H | 98–99° |
| 39 | H | 4-FC$_6$H$_4$ | 4-FC$_6$H$_4$ | CF$_3$ | CH$_3$CH$_2$CH$_2$ | H | H | |
| 40 | H | 4-FC$_6$H$_4$ | 4-FC$_6$H$_4$ | CF$_3$ | CF$_2$CF$_3$ | H | H | |
| 41 | H | 4-FC$_6$H$_4$ | 4-FC$_6$H$_4$ | CF$_3$ | CF$_3$ | 4-NO$_2$C$_6$H$_4$CH$_2$— | H | |
| 42 | H | 4-FC$_6$H$_4$ | 4-FC$_6$H$_4$ | CF$_3$ | CF$_3$ | C$_6$H$_5$CH$_2$— | CH$_3$ | |
| 43 | H | 4-FC$_6$H$_4$ | 4-FC$_6$H$_4$ | CF$_3$ | CF$_3$ | C$_6$H$_5$CH$_2$— | CH$_3$C(=O)— | |
| 44 | H | 4-FC$_6$H$_4$ | 4-FC$_6$H$_4$ | CF$_3$ | CF$_3$ | CH$_3$ | n-C$_6$H$_{13}$C(=O)— | |
| 45 | H | 4-FC$_6$H$_4$ | 4-FC$_6$H$_4$ | CF$_3$ | CF$_3$ | CH$_3$ | 4-NO$_2$C$_6$H$_4$CH$_2$— | |
| 46 | H | 4-FC$_6$H$_4$ | 4-FC$_6$H$_4$ | CF$_3$ | CF$_3$ | CH$_3$ | 4-ClC$_6$H$_4$C(=O)— | |
| 47 | H | 4-FC$_6$H$_4$ | 4-FC$_6$H$_4$ | CF$_3$ | CF$_3$ | CH$_3$ | C$_6$H$_5$OC(=O)— | |
| 48 | H | 4-FC$_6$H$_4$ | 4-FC$_6$H$_4$ | CF$_3$ | CF$_3$ | CH$_3$ | C$_6$H$_5$CH$_2$OC(=O)— | |
| 49 | H | 4-FC$_6$H$_4$ | 4-FC$_6$H$_4$ | CF$_2$CF$_2$CF$_3$ | H | H | H | 91–92° |
| 50 | H | 4-FC$_6$H$_4$ | 4-FC$_6$H$_4$ | CF$_3$ | CH$_3$ | H | H | 102–103° |

Following the procedures given in Examples 1–36, the following intermediate compounds of formula II can be prepared (Table V).

TABLE V

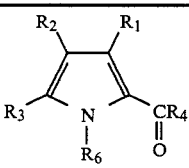

| $R_1$ | $R_2$ | $R_3$ | $R_4$ | $R_6$ | melting point °C. |
|---|---|---|---|---|---|
| H | 4-FC$_6$H$_4$ | 4-FC$_6$H$_4$ | CF$_3$ | H | 211–212 |
| H | 4-CH$_3$OC$_6$H$_4$ | 4-CH$_3$OC$_6$H$_4$ | CF$_2$CF$_3$ | H | 194–195 |
| H | 4-FC$_6$H$_4$ | 4-FC$_6$H$_4$ | CF$_2$CF$_3$ | H | 196–197.5 |
| CH$_3$ | 4-FC$_6$H$_4$ | 4-FC$_6$H$_4$ | CF$_3$ | H | 174–175 |
| H | 4-CH$_3$OC$_6$H$_4$ | 4-CH$_3$OC$_6$H$_4$ | CF$_2$Cl | H | |
| H | 4-FC$_6$H$_4$ | 4-FC$_6$H$_4$ | CF$_2$H | H | |
| H | 4-FC$_6$H$_4$ | C$_6$H$_5$ | CF$_2$CF$_3$ | H | |
| H | 4-FC$_6$H$_4$ | 4-CH$_3$OC$_6$H$_4$ | CF$_2$CF$_3$ | H | |
| C$_2$H$_5$ | 4-FC$_6$H$_4$ | 4-FC$_6$H$_4$ | CF$_3$ | H | |
| H | C$_6$H$_5$ | C$_6$H$_5$ | CF$_3$ | H | 161–162 |
| H | 4-ClC$_6$H$_4$ | 4-ClC$_6$H$_4$ | CF$_3$ | H | 226–227 |
| H | 4-FC$_6$H$_4$ | 4-FC$_6$H$_4$ | CF$_3$ | CH$_3$ | 93–94 |
| H | 4-FC$_6$H$_4$ | 4-FC$_6$H$_4$ | CF$_2$CF$_2$CF$_3$ | H | 189–191 |
| CH$_2$CH$_3$ | 4-CH$_3$OC$_6$H$_4$ | 4-CH$_3$OC$_6$H$_4$ | CF$_2$CF$_3$ | H | |
| H | 4-FC$_6$H$_4$ | 3-pyridyl | CF$_3$ | H | |
| H | C$_6$H$_5$ | 3,4-Cl$_2$C$_6$H$_3$ | CF$_3$ | H | |
| H | 4-FC$_6$H$_4$ | 4-CH$_3$SC$_6$H$_4$ | CF$_3$CF$_2$ | H | |
| H | 4-FC$_6$H$_4$ | 4-(CH$_3$)$_2$NC$_6$H$_4$ | CF$_3$ | H | |
| H | 4-FC$_6$H$_4$ | 4-BrC$_6$H$_4$ | CF$_3$ | H | |
| H | 4-CH$_3$C$_6$H$_4$ | 4-CH$_3$C$_6$H$_4$ | CF$_3$ | H | |

TABLE V-continued

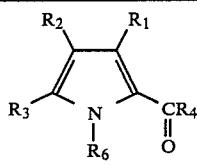

| R₁ | R₂ | R₃ | R₄ | R₆ | melting point °C. |
|---|---|---|---|---|---|
| H | 4-C₂H₅OC₆H₄ | 4-C₂H₅OC₆H₄ | CF₃ | H | |
| H | 4-FC₆H₄ | 4-FC₆H₄ | CF₂H | H | |
| H | 4-FC₆H₄ | 4-FC₆H₄ | CF₂Cl | H | |
| H | 4-FC₆H₄ | 4-FC₆H₄ | CFCl₂ | H | |
| H | 4-FC₆H₄ | 4-FC₆H₄ | CF₃ | C₆H₅CH₂ | |
| H | 4-FC₆H₄ | 4-FC₆H₄ | CF₃ | 4-NO₂C₆H₄CH₂— | |
| H | 4-FC₆H₄ | 4-FC₆H₄ | CF₃ | n-C₆H₁₃— | |

DOSAGE FORMS

The antiarthritic and analgesic agents of this invention can be administered to treat arthritis or alleviate pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptons, kind of concurrent treatment, frequency of treatment, and the effect desired. Usually a daily dosage of active ingredient can be about 0.01 to 40 milligrams per kilogram of body weight. Ordinarily 0.05 to 20, and preferably 0.1 to 4 milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coating for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propylparaben and chlorobutanol.

Suitable pharmaceutical carriers are described in *Remington's Pharmaceutical Sciences,* E. W. Martin, a standard reference text in this field.

Useful pharmaceutical dosage forms for administration of the compounds of this invention can be illustrated as follows:

Capsules

A large number of unit capsules are prepared by filling standard two-piece hard gelatin capsules each with 50 milligrams of powdered active ingredient 175 milligrams of lactose, 24 milligrams of talc, and 6 milligrams magnesium stearate.

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 0.2 milligrams of colloidal silicon dioxide, 5 milligrams of magnesium stearate, 275 milligrams of microcrystalline cellulose, 11 milligrams of cornstarch and 98.9 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by commonly used techniques.

Suspension

An aqueous suspension is prepared for oral administration so that each 5 milliliters contain 10 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Injectable

A parenteral composition suitable for administration by injection is prepared by stirring 1% by weight of active ingredient in sodium chloride injection U.S.P. XV and sterilizing by commonly used techniques.

USE

To detect and compare the anti-inflammatory activities of compounds in this series and standard drugs, a test was used based on a standard model of arthritis for which there is good correlation with human efficacy. The model is adjuvant-induced arthritis in rats. Federation Proceedings, Vol. 32, No. 2,1973, "Models Used for the Study and Therapy of Rheumatoid Arthritis'-'—Symposium of the American Society for Pharmacology and Experimental Therapeutics—states "The rat polyarthritis produced by intradermal injection of a suspension of *Mycobacterium tuberculosis* is mineral oil (adjuvant) has been used extensively for the screening of drugs of potential used in rheumatoid arthritis."

Compounds of this invention have shown activity in adjuvant-induced arthritis in rats which is widely recognized as a good model of human rheumatoid arthritis.

METHODS

Established Adjuvant-Induced Arthritis in Rats

Lewis (Wistar) male rats (Charles River Breeding Laboratories, Wilmington, Mass.) weighing 175-220 grams were injected subcutaneously with 0.1 ml of adjuvant in the plantar area of the right hind paw. The adjuvant was prepared by bead-milling, heat-killed, lyophilized *Mycobacterium butyricum* (Difco #0640) in light mineral oil (Fisher Scientific Co. #0-119 Paraffin Oil-Saybolt Viscosity 125/135) 5 mg/ml. Twenty non-arthritic control rats were injected with mineral oil. The animals received water and Wayne Lab-Blox ad libitum*.

*while on a 10-hour light—14 hour-dark cycle

The rats were held for 14 days to allow the development of polyarthritis. The volume of the uninjected, left-hind paw of each rat was measured by using a Ugo Basile Volume Differential Meter, Model 7101. Adjuvant injected rats showing no evidence of arthritis were discarded and the arthritic rats were distributed into groups of 10 having equal mean paw volumes with equal standard deviation. Non-arthritic (oil-injected) control rats were distributed to 2 groups of 10. Suspension of test compounds were prepared for dosing by bead-milling (4 mm glass beads in rubber stoppered serum bottles) for 4-5 hours in aqueous 1% polyvinyl alcohol, 5% gum acacia and 0.5% methylparaben.

Test compounds were given orally by gavage once daily for 7 days (days 14–20). The 2 groups of oil injected, non-arthritic control rats and the 2 groups of arthritic control rats received vehicle only for 7 days. Paw volumes (uninjected left hind paw) were measured 20 hours after the last dose (on day 21).

Percent decrease from control mean paw volume was calculated with the following formula:

$$\frac{\text{Arthritic Vehicle Control Mean Paw Volume (ml)} - \text{Arthritic Treatment Mean Paw Volume (ml)}}{\text{Arthritic Vehicle Control Mean Paw Volume (ml)} - \text{Non-Arthritic Vehicle Control Mean Paw Volume (ml)}} \times 100 =$$

% Decrease from Control Mean Paw Volume

Dose-response regression lines of the % decrease were plotted on semi-log paper and the $ED_{50}\%$ for decrease from control paw volume was estimated by inspection.

A procedure for detecting and comparing the analgesic activity of compounds in this series and standard drugs for which there is a good correlation with human efficacy is the phenylquinone writhing test.

Phenylquinone Writhing Test

The phenylquinone writhing test, modified from Siegmund, et al., *Proc. Soc. Exp. Biol. Med.*, 95, 729 (1957), was employed. A test compound suspended in 1% methylcellulose was given orally to fasted (17–21 hours) female white mice, 5–20 animals per double blind test. Aqueous (0.01% phenyl-p-benzoquinone) phenylquinone was injected intraperitoneally at 24 minutes later using 0.20 ml per mouse. Commencing at 30 minutes after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Thompson, W. R., *Bact. Rev.*, 11, 115–145 (1947).

RESULTS

The antiarthritic and analgesic activity of some compounds of this invention are summarized in Table VI.

TABLE VI

Antiarthritic and Analgesic Activity

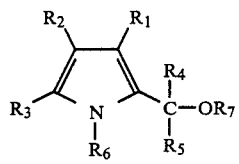

| Example | R$_1$ | R$_2$ | R$_3$ | R$_4$ | R$_5$ | R$_6$ | R$_7$ | Adjuvant Arthritis[1] ED$_{50}$ (mg/kg) | Phenylquinone Writhing ED$_{50}$ (mg/kg) |
|---|---|---|---|---|---|---|---|---|---|
| 1 | H | 4-ClC$_6$H$_4$ | 4-ClC$_6$H$_4$ | CF$_3$ | CF$_3$ | H | H | 7.0 | >108 |
| 2 | H | C$_6$H$_5$ | C$_6$H$_5$ | CF$_3$ | CF$_3$ | H | H | (42%/81) | 135 |
| 3 | H | 4-FC$_6$H$_4$ | 4-FC$_6$H$_4$ | CF$_3$ | CF$_3$ | H | H | 3.5 | >108 |
| 4 | H | C$_6$H$_5$ | 3,4-Cl$_2$C$_6$H$_3$ | CF$_3$ | CF$_3$ | H | H | 70 | >108 |
| 5 | H | 4-FC$_6$H$_4$ | 4-BrC$_6$H$_4$ | CF$_3$ | CF$_3$ | H | H | 6.0 | >135 |
| 6 | CH$_3$ | 4-FC$_6$H$_4$ | 4-FC$_6$H$_4$ | CF$_3$ | CF$_3$ | H | H | 2.8 | >135 |
| 7 | H | C$_6$H$_5$ | 3-pyridyl | CF$_3$ | CF$_3$ | H | H | (31%/18) | 78 |
| 8 | H | 4-CH$_3$OC$_6$H$_4$ | 4-CH$_3$OC$_6$H$_4$ | CF$_3$ | CF$_3$ | H | H | 4.0 | 5.2 |
| 9 | H | 4-CH$_3$C$_6$H$_4$ | 4-CH$_3$C$_6$H$_4$ | CF$_3$ | CF$_3$ | H | H | 8.0 | >108 |
| 10 | H | 4-FC$_6$H$_4$ | 4-(CH$_3$)$_2$NC$_6$H$_4$ | CF$_3$ | CF$_3$ | H | H | 2.2 | >108 |
| 11 | H | 4-FC$_6$H$_4$ | 3-pyridyl | CF$_3$ | CF$_3$ | H | H | (47%/15) | >108 |
| 12 | H | 4-FC$_6$H$_4$ | 4-CH$_3$SC$_6$H$_4$ | CF$_3$ | CF$_3$ | H | H | 9.0 | >108 |
| 13 | H | 4-FC$_6$H$_4$ | 4-CH$_3$SO$_2$C$_6$H$_4$ | CF$_3$ | CF$_3$ | H | H | (22%/27) | >108 |
| 16 | H | 4-FC$_6$H$_4$ | 4-FC$_6$H$_4$ | —CF$_2$CF$_2$CF$_2$— | | H | H | 1.3 | >108 |
| 17 | H | 4-FC$_6$H$_4$ | 4-FC$_6$H$_4$ | CF$_2$Cl | CF$_2$Cl | H | H | 6.5 | >108 |
| 18 | H | 4-FC$_6$H$_4$ | 4-FC$_6$H$_4$ | CHF$_2$ | CF$_3$ | H | H | 4.0 | >108 |
| 19 | H | 4-FC$_6$H$_4$ | 4-FC$_6$H$_4$ | CF$_2$Cl | CF$_3$ | H | H | 2.0 | >108 |
| 20 | H | 4-FC$_6$H$_4$ | 4-FC$_6$H$_4$ | —CF$_2$CF$_2$CFCl— | | H | H | 4.5 | >108 |
| 21 | H | 4-FC$_6$H$_4$ | 4-FC$_6$H$_4$ | —CF$_2$CF$_2$CFBr— | | H | H | 20 | >108 |
| 22 | H | 4-FC$_6$H$_4$ | 4-FC$_6$H$_4$ | CF$_2$Cl | CFCl$_2$ | H | H | 7.0 | >108 |
| 28 | H | 4-FC$_6$H$_4$ | 4-FC$_6$H$_4$ | CF$_3$ | CF$_3$ | CH$_3$ | H | 0.66 | 45 |
| 29 | H | 4-FC$_6$H$_4$ | 4-FC$_6$H$_4$ | CF$_3$ | H | H | H | 11 | >108 |
| 30 | H | 4-CH$_3$OC$_6$H$_4$ | 4-CH$_3$OC$_6$H$_4$ | CF$_3$ | H | H | H | 5.5 | 13.4 |
| 31 | H | 4-CH$_3$OC$_6$H$_4$ | 4-CH$_3$OC$_6$H$_4$ | CF$_3$ | CH$_3$ | H | H | 1.25 | 23 |
| 32 | H | 4-FC$_6$H$_4$ | 4-FC$_6$H$_4$ | CF$_3$ | CF$_3$ | CH$_3$ | CH$_3$ | 5.5 | >108 |
| 33 | H | 4-FC$_6$H$_4$ | 4-FC$_6$H$_4$ | CF$_3$ | CF$_3$ | H | CH$_2$C$_6$H$_5$ | (35%/25) | — |
| 34 | H | 4-FC$_6$H$_4$ | 4-FC$_6$H$_4$ | CF$_3$ | CF$_3$ | CH$_3$ | $\overset{\text{O}}{\overset{\|}{\text{C}}}$CH$_3$ | 2.5 | >108 |
| 35 | H | 4-FC$_6$H$_4$ | 4-FC$_6$H$_4$ | CF$_3$ | CF$_3$ | CH$_3$ | $\overset{\text{O}}{\overset{\|}{\text{C}}}$C$_6$H$_5$ | (22%/27) | >108 |
| 36 | H | 4-FC$_6$H$_4$ | 4-FC$_6$H$_4$ | CF$_3$ | CF$_3$ | CH$_3$ | COCH$_3$ (C=O) | (46%/25) | >108 |
| 37 | H | 4-FC$_6$H$_4$ | 4-FC$_6$H$_4$ | CF$_2$CF$_3$ | H | H | H | 2.9 | 103 |
| 38 | H | 4-FC$_6$H$_4$ | 4-FC$_6$H$_4$ | CF$_2$CF$_3$ | CH$_3$ | H | H | 3.1 | >108 |
| 49 | H | 4-FC$_6$H$_4$ | 4-FC$_6$H$_4$ | CF$_2$CF$_2$CF$_3$ | H | H | H | 7.0 | >108 |
| 50 | H | 4-FC$_6$H$_4$ | 4-FC$_6$H$_4$ | CF$_3$ | CH$_3$ | H | H | (47%/9) | >108 |

[1] Values in parentheses represent the percent reduction in paw volume at the indicated dose.

What is claimed is:

1. A compound of the formula

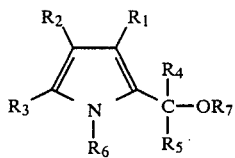

wherein
R$_1$=H or C$_1$-C$_2$ alkyl;
R$_2$ and R$_3$ independently=3-pyridyl or

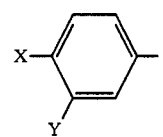

where
X=H, F, Cl, Br, C$_1$-C$_2$ alkyl, C$_1$-C$_2$ alkoxy, di(C$_1$-C$_2$ alkyl)amino or CH$_3$S(O)$_n$ where
n=0, 1 or 2; and
Y=H, F or Cl;
with the proviso that when Y is F or Cl, then X is F or Cl;
R$_4$ and R$_5$ independently=H, CF$_3$, CF$_2$H, CFCl$_2$, CF$_2$Cl, CF$_2$CF$_3$, C$_1$-C$_3$ alkyl or CF$_2$CF$_2$CF$_3$;

with the provisos (1) that no more than one of $R_4$ or $R_5$ can be selected from the group consisting of H and $C_1$-$C_3$ alkyl, (2) that no more than one of $R_4$ or $R_5$ can be $CF_2CF_3$ and (3) that when one of $R_4$ or $R_5$ is $CF_2CF_2CF_3$, then the other $R_4$ or $R_5$ must be H; or $R_4$ and $R_5$ taken together=$CF_2CF_2CFZ$—,
where
Z=F, Cl or Br;
$R_6$=H; $C_1$-$C_6$ alkyl;
$R_7$=H, $C_1$-$C_6$ alkyl; benzyl; benzyl substituted by up to three substituents, where said substituents are independently selected from F, Cl, Br, $NO_2$, $CF_3$ $C_1$-$C_2$ alkyl, or $C_1$-$C_2$ alkoxy;

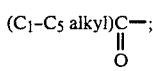

benzoyl; or benzoyl substituted by up to three substituents, where said substituents are independently selected from F, Cl, Br, $NO_2$, $CF_3$, $C_1$-$C_2$ alkyl, or $C_1$-$C_2$ alkoxy; or —$COOR_8$;
$R_8$=$C_1$-$C_4$ alkyl; phenyl; phenyl substituted by up to three substituents, where said substituents are independently selected from F, Cl, Br, $NO_2$, $CF_3$, $C_1$-$C_2$ alkyl, or $C_1$-$C_2$ alkoxy; benzyl or benzyl substituted by up to three substituents, where said substituents are independently selected from F, Cl, Br, $NO_2$, $CF_3$, $C_1$-$C_2$ alkyl, or $C_1$-$C_2$ alkoxy;
with the proviso that $R_6$ cannot be H when $R_7$ is alkanoyl, benzoyl or substituted benzoyl, or $COOR_8$; or a pharmaceutically suitable acid addition salt where $R_2$ or $R_3$ is 3-pyridyl or X is dialkylamino; or a pharmaceutically suitable metal salt when $R_7$ is H.

2. A compound of claim 1 $R_4$ and $R_5$ independently=$CF_3$, $CF_2H$ or $CF_2Cl$; or $R_4$ and $R_5$ taken together=—$CF_2CF_2CF_2$—; $R_6$=H; and $R_7$=H.

3. A compound of claim 1 where $R_1$=H or methyl.

4. A compound of claim 1 where $R_2$ and $R_3$ independently=

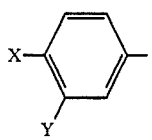

where X=Cl, F, methoxy or dimethylamino and Y=H.

5. A compound of claim 1 where $R_4$ and $R_5$ are both $CF_3$.

6. A compound of claim 1 where $R_6$=H or methyl.

7. A compound of claim 1 where $R_7$=H.

8. A compound of claim 1 where
$R_1$=H or methyl;
$R_2$ and $R_3$ independently=

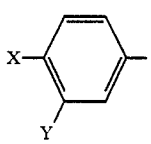

where X=Cl, F, methoxy or dimethylamino and Y=H;

$R_4$ and $R_5$ are both $CF_3$;
$R_6$=H or methyl; and
$R_7$=H.

9. The compound of claim 1 which is 4,5-bis(4-fluorophenyl)-α,α-bis(trifluoromethyl)-1H-pyrrole-2-methanol.

10. The compound of claim 1 which is 4-(4-fluorophenyl)-5-(4-dimethylaminophenyl)-α,α-bis(trifluoromethyl)-1H-pyrrole-2-methanol.

11. The compound of claim 1 which is 4,5-bis-(4-fluorophenyl)-1-methyl-α, α-bis(trifluoromethyl)-1H-pyrrole-2-methanol.

12. A pharmaceutical composition consisting essentially of a suitable pharmaceutical carrier and an effective antiinflammatory amount of a compound of claim 1.

13. A pharmaceutical composition consisting essentially of a suitable pharmaceutical carrier and an effective antiinflammatory amount of a compound of claim 2.

14. A pharmaceutical composition consisting essentially of a suitable pharmaceutical carrier and an effective antiinflammatory amount of a compound of claim 3.

15. A pharmaceutical composition consisting essentially of a suitable pharmaceutical carrier and an effective antiinflammatory amount of a compound of claim 4.

16. A pharmaceutical composition consisting essentially of a suitable pharmaceutical carrier and an effective antiinflammatory amount of a compound of claim 5.

17. A pharmaceutical composition consisting essentially of a suitable pharmaceutical carrier and an effective antiinflammatory amount of a compound of claim 6.

18. A pharmaceutical composition consisting essentially of a suitable pharmaceutical carrier and an effective antiinflammatory amount of a compound of claim 7.

19. A pharmaceutical composition consisting essentially of a suitable pharmaceutical carrier and an effective antiinflammatory amount of a compound of claim 8.

20. A pharmaceutical composition consisting essentially of a suitable pharmaceutical carrier and an effective antiinflammatory amount of the compound of claim 9.

21. A pharmaceutical composition consisting essentially of a suitable pharmaceutical carrier and an effective antiinflammatory amount of the compound of claim 10.

22. A pharmaceutical composition consisting essentially of a suitable pharmaceutical carrier and an effective antiinflammatory amount of the compound of claim 11.

23. A method of treating inflammation in a mammal which comprises administering to the mammal an antiinflammatory amount of a compound of claim 1.

24. A method of treating inflammation in a mammal which comprises administering to the mammal an antiinflammatory amount of a compound of claim 2.

25. A method of treating inflammation in a mammal which comprises administering to the mammal an antiinflammatory amount of a compound of claim 3.

26. A method of treating inflammation in a mammal which comprises administering to the mammal an antiinflammatory amount of a compound of claim 4.

27. A method of treating inflammation in a mammal which comprises administering to the mammal an anti-inflammatory amount of a compound of claim 5.

28. A method of treating inflammation in a mammal which comprises administering to the mammal an anti-inflammatory amount of a compound of claim 6.

29. A method of treating inflammation in a mammal which comprises administering to the mammal an anti-inflammatory amount of a compound of claim 7.

30. A method of treating inflammation in a mammal which comprises administering to the mammal an anti-inflammatory amount of a compound of claim 8.

31. A method of treating inflammation in a mammal which comprises administering to the mammal an anti-inflammatory amount of the compound of claim 9.

32. A method of treating inflammation in a mammal which comprises administering to the mammal an anti-inflammatory amount of the compound of claim 10.

33. A method of treating inflammation in a mammal which comprises administering to the mammal an anti-inflammatory amount of the compound of claim 11.

* * * * *